United States Patent [19]

Roduit et al.

[11] Patent Number: 5,446,162
[45] Date of Patent: Aug. 29, 1995

[54] PROCESS FOR THE PRODUCTION OF 7-ACYLINDOLES

[75] Inventors: Jean-Paul Roduit, Sierre; Alain Wellig, Ried-Mörel, both of Switzerland

[73] Assignee: Lonaz Ltd., Gampel/Valais, Switzerland

[21] Appl. No.: 280,738

[22] Filed: Jul. 26, 1994

Related U.S. Application Data

[62] Division of Ser. No. 84,168, Jun. 30, 1993, Pat. No. 5,380,857.

[30] Foreign Application Priority Data

Jul. 2, 1992 [CH] Switzerland ............. 2083/92

[51] Int. Cl.$^6$ ........................................ C07D 401/06
[52] U.S. Cl. .................... 546/273; 548/468; 548/490
[58] Field of Search ............... 546/273; 548/490, 468

[56] References Cited

U.S. PATENT DOCUMENTS 4,221,716  9/1980  Lo et al. .............................. 548/510
5,120,749  6/1992  Summers et al. ................... 514/337

FOREIGN PATENT DOCUMENTS 181136   5/1986   European Pat. Off. .
395528  10/1990   European Pat. Off. .

OTHER PUBLICATIONS

CA 116:143891, Ward 1992.
CA 90:151918 Ivanova et al. 1979.
Oldroyd et al. J. Photochem. Photobiol. 1991. 57(1–3). 207–16. as CA abstract.
Walsh et al. J. Med. Chem. 1984. 27(11). 1379–88 as CA Abstract.
Kim et al. J. Heterocycl. Chem. 1981. 18(7). 1365–71 as CA abstract.

*Primary Examiner*—Jane Fan
*Attorney, Agent, or Firm*—Fisher, Christen & Sabol

[57] ABSTRACT

A process for the production of 7-acylindoles of the general formula:

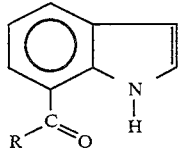

starting from indoline of the formula:

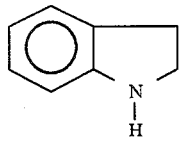

Indoline is cyanized in a first stage to 7-cyanoindoline of the formula:

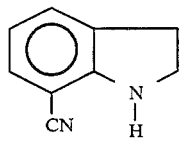

The latter is catalytically dehydrogenated in a second stage to 7-cyanindole of the formula:

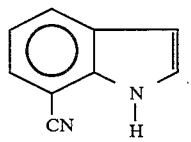

The latter is then acylated in a third stage with an organometallic compound of the formula:

R—Q                                V into the end product according to formula I.

5 Claims, No Drawings

PROCESS FOR THE PRODUCTION OF 7-ACYLINDOLES

This is a divisional application of Ser. No. 08/084,168, filed Jun. 30, 1993, now U.S. Pat. No. 5,380,857 issued Jan. 10, 1995.

BACKGROUND OF THE INVENTION

1. Field Of The Invention

The invention relates to a new process for the production of 7-acylindoles of the general formula:

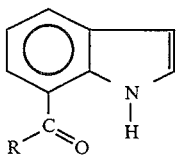
I wherein R means a $C_1$-$C_4$-alkyl-, $C_2$-$C_4$-alkenyl-, $C_2$-$C_4$-alkinyl-, aryl- or heteroaryl group, starting from indoline of the formula:

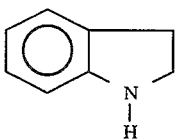
II

2. Background Art

A process for the production of 7-acylindoles starting from indoline is known [Walsh et al., J. Med. Chem., Vol. 27, No. 11, (1984), pp. 1379 to 1388].

In the process indoline is first converted with a halogenated benzonitrile as an acylation agent into 7-acylindoline, which is then thermally dehydrogenated in the presence of manganese(IV)-oxide to 7-acylindole. A great drawback of the process is that, on the one hand, the feedstocks (the halogenated benzonitrile) are difficult to obtain chemically and, on the other hand, the process is feasible neither ecologically nor on a large scale.

BROAD DESCRIPTION OF THE INVENTION

The main object of the invention is to provide a process for the production of 7-acylindoles that is feasible ecologically and on a large scale, in which the products are obtained in good yield. Other objects and advantages of the invention are set out herein or are obvious herefrom to one skilled in the art.

The objects and advantages of the invention are achieved by the process and compounds of the invention.

The invention includes a process for the production of 7-acylindoles of the general formula:

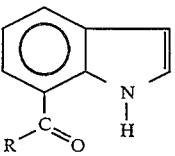
I wherein R means a $C_1$-$C_4$-alkyl-, $C_2$-$C_4$-alkenyl-, $C_2$-$C_4$-alkinyl-, aryl- or heteroaryl group. In the first stage, indoline of the formula:

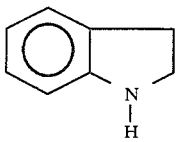
II is cyanized to 7-cyanoindoline of the formula:

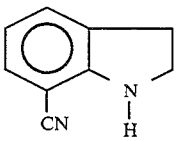
III

The latter is catalytically dehydrogenated in the second stage to a 7-cyanoindole of the formula:

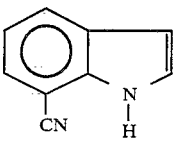
IV

The latter, in the third stage, is then acylated with an organometallic compound of the general formula:

R—Q         V wherein R has the above-mentioned meaning and Q means a metal atom or a group M-X, wherein M means an alkaline-earth metal, copper or zinc and X means chlorine, bromine or iodine, into the end product according to formula I.

Preferably the cyanization in the first stage is performed in two steps by reaction of the indoline with a Lewis acid with trichloracetonitrile and then by treatment of the intermediary intermediate products with an alkali metal alcoholate. Preferably the cyanization in the first stage is performed at a temperature of 40° to 100° C. Preferably palladium, optionally applied on a suitable carrier is used as dehydrogenation catalyst in the second stage. Preferably the dehydrogenation in the second stage is performed in a high-boiling organic solvent. Preferably the dehydrogenation in the second stage is performed at a temperature of 130° C. to reflux temperature. Preferably the dehydrogenation in the second stage is performed in the presence of a benzyl ester of the general formula:

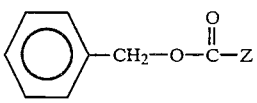
VI wherein Z means a $C_1$-$C_4$-alkyl group. Preferably one of the organometallic compounds of formulas R-M-X, wherein M means an alkaline-earth metal and X means chlorine, bromine or iodine, is used for the acylation in the third stage as organometallic compound R—Q. Preferably the acylation in the third stage is performed in the presence of a strong base. Preferably an alkali metal hydride, an alkali metal amide or an alkali metal alkoxide is used as a strong base in the third stage. Preferably the acylation in the third stage is performed at a temperature of −20° to 30° C.

The invention also includes 7-acylindoles of the general formula:

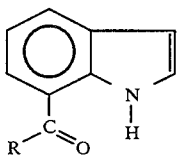

I wherein R means a butyl-, 4-tertiarybutyl-phenyl-, pyridinyl- or thienyl group.

7-Acylindoles are important intermediate products for the production of pharmaceutical agents. For example, 7-(4-bromobenzoyl)indole is an important intermediate product for the production of 7-(4-bromobenzoyl)oxoindole derivatives which, in turn, represent important intermediate products for the production of anti-inflammatory pharmaceutical agents (J. Med. Chem., Vol. 27, No. 11, (1984), pp. 1379 to 1388).

DETAIL DESCRIPTION OF THE INVENTION

According to the invention the process is performed so that in the first stage an indoline of the formula:

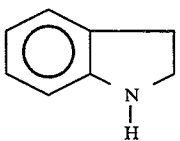

II is cyanized to 7-cyanoindoline of the formula:

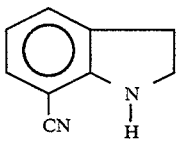

III

The latter is catalytically dehydrogenated in the second stage to a 7-cyanoindole of the formula:

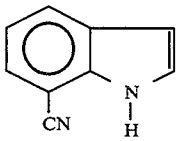

IV

The latter, in the third stage, is then acylated with a organometallic compound of general the formula:

 R—Q

V wherein R has the above-mentioned meaning and Q means a metal atom or a group-M-X, wherein M means an alkaline-earth metal, copper or zinc and X means chlorine, bromine or iodine, into the end product according to formula I.

The first stage, the cyanization of the indoline to the 7-cyanoindoline, suitably takes place in two steps by reaction of the indoline with a Lewis acid with a cyanization agent and then treatment of the intermediary intermediate product with a alkali metal alcoholate. Trichloroacetonitrile, cyanogen chloride, methylthiocyanate or N-cyanimidazole can be used as the cyanization agent. Preferably trichloroacetonitrile is used as cyanization agent. Suitably the cyanization agent is used in excess relative to the indoline, preferably in an amount of 1.5 to 2.2 mol relative to 1 mol of the indoline.

As the Lewis acid, for example, boron trichloride, boron tribromide, boron trifluoride and/or silicon tetrachloride can be used, preferably boron trichloride is used. Suitably the Lewis acid is used in excess relative to the indoline, preferably in an amount of 1 to 1.5 mol relative to 1 mol of the indoline. As the alkali metal alcoholate, for example, sodium methanolate, sodium ethanolate or potassium methanolate, potassium ethanolate can be used. Preferably sodium methanolate is used. Suitably the alkali metal alcoholates are used in an amount of 2 to 4 mol, preferably 2.0 to 2.5 mol, relative to 1 mol of the indoline. Suitable solvents for the cyanization in the first step are toluene, benzene, xylene or chloroform, and preferably is toluene. In the second step of the cyanization the subsequent treatment of the intermediary intermediate products with an alkali metal alcoholate then usually takes place in the corresponding alcohol as solvent. Suitably the cyanization is performed at a temperature of 40° to 100° C., preferably 50° to 65° C.

Then, after a usual reaction time of 12 to 24 hours, the 7-cyanoindoline of formula III can be isolated according to methods usual to one skilled in the art.

The second stage, that is, the dehydrogenation of the 7-cyanoindoline to the 7-cyanoindole of formula IV, takes place catalytically. As the dehydrogenation catalysts, noble metal catalysts, such as, platinum, palladium or rhodium catalysts, optionally applied to a suitable carrier can be used. Suitably the catalytic dehydrogenation is performed with palladium, optionally applied to a suitable carrier. As the carrier, for example, carbon or aluminum oxide are suitable. Preferably palladium on aluminum oxide, especially 5 to 10 percent by weight of palladium on aluminum oxide, is used as the dehydrogenation catalyst. The dehydrogenation catalyst can be used in an amount of 0.001 to 0.01 mol, preferably of 0.003 to 0.005 mol, per mole of the 7-cyanoindoline.

In an especially preferred embodiment the catalytic dehydrogenation is performed in the presence of a benzyl ester of the general formula:

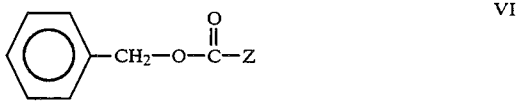

VI wherein Z means a $C_1$-$C_4$-alkyl group. Suitable representatives of these benzyl esters are benzyl acetate, benzyl propionate and benzyl butanoate. Preferably benzyl acetate is used as the benzyl ester. Suitably the benzyl ester is used equimolar to the 7-cyanoindoline.

High-boiling organic solvents, such as, dekalin, p-cymol or xylene, are used as solvents for the catalytic dehydrogenation. Preferably dekalin is used as the solvent.

The catalytic dehydrogenation suitably takes place at a temperature of 130° C. up to the reflux temperature of the solvent, preferably of 150° C. up to the reflux temperature. Usually the catalytic dehydrogenation is performed under an inert gas atmosphere.

After a usual reaction time of 2 to 4 hours, the 7-cyanoindole can then be isolated according to methods usual to one skilled in the art.

In the third stage, the 7-cyanoindole is acylated with a organometallic compound of the general formula:

wherein R has the above-mentioned meaning and Q means a metal atom or a group-M-X, wherein M means an alkaline-earth metal, copper or zinc and X means chlorine, bromine or iodine, into a 7-acylindole of the formula I.

An alkali or alkaline-earth metal atom can be used as the metal atom. If Q means an alkali metal atom, for example, lithium or sodium can be used as the alkali metal. If Q means a alkaline-earth metal atom, for example, magnesium or calcium can be used as the alkaline-earth metal. If Q means a group M-X, for example, magnesium or calcium can be used as the alkaline-earth metal. Preferably Q means a group M-X, in which M means magnesium and X means bromine or chlorine.

Suitable radicals R of the organometallic compound R—Q are:
- if R means a $C_1$–$C_4$-alkyl group, methyl, ethyl, propyl, isopropyl, butyl or isobutyl
- if R means a $C_2$–$C_4$-alkenyl group, ethenyl, propenyl or butenyl
- if R means a $C_2$–$C_4$-alkinyl group, ethinyl, propinyl or butinyl
- if R means a aryl group, phenyl or naphthyl, optionally ring-substituted with a halogen atom, such as, bromine or chlorine, or ring-substituted with a $C_1$–$C_4$-alkyl group, branched or unbranched, such as, a tertiary butyl group
- if R means a heteroaryl group, pyridinyl, pyrazinyl or thiophenyl.

Preferred representatives of organometallic compounds R—Q wherein Q means magnesium bromide, are:
butyl magnesium bromide (R=butyl)
phenyl magnesium bromide (R=phenyl)
4-chlorophenyl magnesium bromide (R=chlorophenyl)
4-bromophenyl magnesium bromide (R=4-bromophenyl)
4-tertiarybutyl-phenyl magnesium bromide (R=tertiarybutylphenyl)
2-pyridinyl-magnesium bromide (R=pyridinyl)
2-thienyl-magnesium bromide (R=thienyl).

These organometallic compounds can be formed according to methods usual to one skilled in the art from the corresponding alkyl, alkenyl, alkinyl, aryl or heteroaryl halides by reaction with magnesium. Suitably the organometallic compounds R—Q are used in an amount of 1 to 2.5 mol, preferably of 1 to 1.5 mol, per mol of the 7-cyanoindole.

Optionally it can be advantageous to perform the reaction in the third stage in the presence of a strong base. For example, alkali metal hydrides, alkali metal amides or alkali metal alkoxides are suitable as the strong base. Sodium or potassium hydride can be used as the alkali metal hydride and sodium or potassium amide can be used as the alkali metal amide. Sodium or potassium methanolate, ethanolate or butanolate can be used as the alkali metal alkoxide. Preferably an alkali metal hydride, such as, sodium hydride is used as the strong base. Suitably the strong base is used in a slight excess relative to the 7-cyanoindole. Preferably the strong base is used in an amount of 1 to 1.1 mol per mole of the 7-cyanoindole.

A special advantage in using a strong base is that the amount of organometallic compound to be used can be reduced. Accordingly, then the organometallic compound is suitably used in an amount of 1 to 1.5 mol per mole of the 7-cyanoindole.

Suitable solvents for the third stage are cyclic ethers, such as, tetrahydrofuran, dialkyl ethers, such as, diethyl ether, toluene, benzene and mixtures thereof.

Preferably a mixture of tetrahydrofuran and toluene is used as the solvent. Suitably the reaction in the third stage is performed at a temperature of −20° to 30° C., preferably 0° to 25° C. and usually under an inert gas atmosphere After a usual reaction time of 0.5 to 3 hours, the 7-acylindoles according to the general formula:

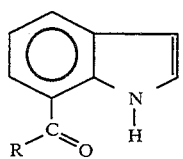

wherein R has the above-mentioned meaning, are then obtained by acid hydrolysis usual to one skilled in the art. Preferred representatives of the 7-acylindoles are:
7-benzoylindole (R=phenyl)
7-(4-chlorobenzoyl)indole (R=4-chlorophenyl)
7-(4-bromobenzoyl)indole (R=4-bromophenyl) as well as those so far not yet described in the literature:
7-butanoylindole (R=butyl)
7-(4-tertiarybutyl-benzoyl)indole (R=4-tertiarybutyl-phenyl)
7-(2-pyridinecarbonyl)-indole (R=2-pyridinyl)
7-(2-thienecarbonyl)-indole (R=2-thienyl)

The 7-acylindoles not yet described in the literature are also a component of the invention.

EXAMPLE 1

(a) Production of 7-cyanoindoline 22 g of $BCl_3$ (187.8 mmol) in 120 ml of toluene (dried) was dissolved in a 750 ml round flask at −20°. 15.9 g of indoline (133.4 mmol) in 100 ml of toluene was added within 25 minutes and the temperature rose to 10°. This suspension was refluxed for 1 hour, then 110 ml of toluene was distilled off and the reaction mixture was cooled to 55° C. Then 38.4 g of trichloroacetonitrile (266 mmol) was added within 20 minutes and the resulting red solution was stirred for 20 hours at 60° C. After addition of methanol (110 ml) the reaction mixture was mixed within 1.5 hours with 60 g of a 30 percent methanolic sodium methanolate solution. After 1 hour of stirring the methanol was distilled off in a vacuum and then toluene (300 ml) and water (300 ml) were added. The aqueous phase was extracted several times with 200 ml of toluene. The combined toluene extracts were then washed with a 0.12N HCl (91 ml) and with water to remove the not reacted indoline. After concentration by evaporation of toluene 20.12 g of a brownish oil was obtained. The latter was then recrystallized in a hexane/pentanol mixture (80 ml; mixture ratio of hexane:pentanol=9:7) to obtain 11.47 g of a light brownish product with a purity of 99.4 percent corresponding to a yield of 60.5 percent relative to feedstock used. Other data concerning the product was:

$^1$H-NMR (CDCl$_3$) δ in ppm: 3.08, t; 3.70, t; 4.53 bs, 6.61, t; 7.13, d; 7.18, d.

(b) Production of 7-cyanoindole

A mixture of 1.2 g of 7-cyanoindoline (8.3 mmol) and 1.25 g of benzyl acetate (8.3 mmol) in dekalin (20 ml) was heated under inert gas atmosphere to 75° C. 0.15 g of 5 percent Pd/Al$_2$O$_3$ catalyst (Degussa type E 207 RID) was added to this mixture and all of this was heated at reflux temperature for 3.3 hours. Then the catalyst was filtered off and washed with toluene (5 ml). After concentration by evaporation of the solvent, 1.19 g of solid material was obtained, containing 98.3 percent of 7-cyanoindole and 0.7 percent of 7-cyanoindoline. Pure 7-cyanoindole was obtained by crystallization from an n-hexane-xylene mixture (mixture ratio of n-hexane: xylene=7:2). 0.94 g of product corresponding to a yield of 79.7 percent relative to 7-cyanoindoline used was obtained. The product had a melting point of 102.2° to 103.2° C. Other data concerning the product was:

$^1$H-NMR (CDCl$_3$) δ in ppm: 6.66, m; 7.36, m; 7.55, d; 7.18, t; 7.89, d; 9.08, bs.

(c) Production of 7-(4-tertiary-butyl-benzoyl)indole 2 g of 7-cyanoindole (14.1 mmol) in tetrahydrofuran (10 ml) and toluene (15 ml) was heated under inert gas atmosphere to 20° C. Then sodium hydride (0.38 g; 15 mmol; quality: 95 percent) was added to facilitate the deprotonation. Then 4-tertiary-butyl-magnesium bromide [produced from 4.55 g of 1-bromo-4-tertiarybutyl-benzene (20.5 mmol) and 0.67 g of magnesium (27.6 mmol) in tetrahydrofuran] was added to this mixture within 30 minutes at 25° C. This mixture was slowly stirred for 1 hour at 30° C. and then adjusted to a pH of 0.5 with 2N HCl for extraction. The organic phase was washed with common salt solution to obtain 4.2 g of yellow solid after concentration by evaporation. After the recrystallization with ethyl acetate (20 ml), 2.48 g of yellow crystalline product, corresponding to a yield of 67 percent relative to 7-cyanoindole used, was obtained. The product had a melting point of 174° to 175° C. Other data concerning the product was:

$^1$H-NMR (CDCl$_3$) δ in ppm: 1.38, s; 6.65, m; 7.16, t; 7.38, m; 7.53, d; 7.66, d; 7.74, d; 7.92, d; 10.43, bs.

EXAMPLES 2 to 4

7-(2-pyridine carbonyl) indole, 7-(4-chlorobenzoyl)indole and 7-(4-bromobenzoyl)indole were produced analogously to Example 1 (c).

Example 2

7-(2-Pyridine carbonyl)indole:

Yield: crude 84 percent (dark oil) Melting point: 79.5° to 80.5° C. (yellow crystals, recrystallized from diisopropyl ether)

$^1$H-NMR (CDCl$_3$) δ in ppm: 6.66 m; 7.18, t; 7.38, m; 7.48, m; 7.87-7.97 m; 7,95, d; 8.14, d; 8.77, d; 10.54, bs.

Example 3

7-(4-chlorobenzoyl)indole:

Yield: crude 59 percent (brown oil), pure 26 percent (light yellow crystals recrystallized from ethyl acetate) Melting point: 148° to 149° C. $^1$H-NMR (CDCl$_3$) δ in ppm: 6.66, m; 7.16, t; 7.39, m; 7.49, d; 7.56, d; 7.66, d; 7.94, d; 10.38, bs.

Example 4

7-(4-bromobenzoyl)indole:

Yield: crude 60 percent (brown crystalline substance) Melting point: 162.3° to 163.8° C. (light yellow crystals from ethyl acetate) $^1$H-NMR (CDCl$_3$) δ in ppm: 6.66, t; 7.16, t; 7.37, m; 7.55, d; 7.65, s; 7.94, d; 10.39, bs.

EXAMPLE 5

Production of 7-(4-bromobenzoyl)indole

It was possible to achieve a better yield of this product when 1 equivalent of LiCl was additionally added to 1 equivalent of 7-cyanoindole. The reaction conditions were otherwise maintained corresponding to Example 1 (c).

3.76 g of product was obtained with a content of 81 percent as brown crystalline substance corresponding to a yield of 77 percent relative to 7-cyanoindole used.

EXAMPLE 6

Production of 7-(2-thienecarbonyl)indole 2 g of 7-cyanoindole (14.1 mmol) in tetrahydrofuran (10 ml) and toluene (15 ml) was introduced in a round flask at 20° C. under inert gas atmosphere. 2-Thienyl magnesium bromide [produced from 6.21 g of 2-bromothiophene (36.8 mmol) and 1.2 g of magnesium (49.4 mmol) in tetrahydrofuran (53 ml)] was added to the above within 5 minutes. The temperature of the reaction mixture was then maintained for 1 hour at 35° C. and then for another 4.5 hours at 45° C. Then the pH of the mixture was adjusted to 0.5 with a 10 percent sulfuric acid and stirred at 45° C. for 45 minutes. It was extracted after neutralization with 30 percent NaOH. Then the organic phase was washed twice with common salt solution (50 ml) and then concentrated by evaporation to a dark brown oil (3.52 g). The latter was dissolved in ethyl acetate (50 ml), then treated with activated carbon and then this solution was concentrated to 20 ml. All of this was cooled to −50° C. for crystallization. 1.2 g of crystallized product was obtained corresponding to a yield of 38 percent relative to 7-cyanoindole used. The product had a melting point of 128.7° to 129.5° C. (light brown crystals). Other data concerning the product was:

$^1$H-NMR (CDCl$_3$) δ in ppm: 6.65, m; 7.18, m; 7.20, m; 7.37, m; 7.70, d; 7.79, d; 7.93, d; 7.96, m; 10.24 bs.

EXAMPLES 7 TO 8

7-Benzoylindole and 7-butanoylindole were produced analogously to Example 6.

Example 7

7-Butanoylindole:

Yield: crude 73 percent (as waxy substance) Melting point: 67.2° to 68.2° C. (light yellow crystals from ethyl acetate) $^1$H-NMR (CDCl$_3$) δ in ppm: 1.0, t; 1.47, m; 1.8, q; 3.11, t; 6.60, m; 7.18, t; 7.34, m; 7.83, d; 7.90, d; 10.53, bs.

Example 8

7-Benzoylindole:

Yield: crude 96 percent (yellow oil) pure 39 percent (light yellow crystals from ethyl acetate) Melting point: 103° to 104° C. $^1$H-NMR (CDCl$_3$) δ in ppm: 6.66, m; 7.16, t; 7.39, m; 7.53, m; 7.56, d; 7.61, m; 7.78, m; 7.93, d; 10.44, bs.

What is claimed is:

1. A 7-acylindole of formula:

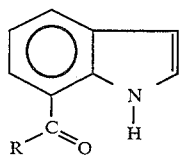

wherein R is butyl, 4-tertiarybutyl-phenyl, pyridinyl or thienyl.

2. The 7-acylindole of formula I as claimed in claim 1 wherein R is butyl.

3. The 7-acylindole of formula I as claimed in claim 1 wherein R is 4-tertiarybutyl-phenyl.

4. The 7-acylindole of formula I as claimed in claim 1 where R is pyridinyl.

5. The 7-acylindole of formula I as claimed in claim 1 wherein R is thienyl.

* * * * *